US00PP18895P2

(12) United States Plant Patent
Tupy et al.

(10) Patent No.: US PP18,895 P2
(45) Date of Patent: Jun. 10, 2008

(54) APPLE TREE NAMED 'RED TOPAZ'

(50) Latin Name: *Malus domestica*
Varietal Denomination: Red Topaz

(75) Inventors: Jaroslav Tupy, Prague (CZ); Otto Louda, Pencin u Liberce (CZ)

(73) Assignee: Institute of Experimental Botany, Prague (CZ)

( * ) Notice: Subject to any disclaimer, the term of this patent is extended or adjusted under 35 U.S.C. 154(b) by 0 days.

(21) Appl. No.: 11/364,358

(22) Filed: Feb. 27, 2006

Related U.S. Application Data

(60) Provisional application No. 60/657,522, filed on Feb. 28, 2005.

(51) Int. Cl.
*A01H 5/00* (2006.01)

(52) U.S. Cl. ..... Plt./161

(58) Field of Classification Search ..... Plt./161
See application file for complete search history.

(56) References Cited

U.S. PATENT DOCUMENTS

PP4,824 P * 2/1982 Lautz ..... Plt./161

PP11,604 P * 10/2000 Easton ..... Plt./161

OTHER PUBLICATIONS

UPOV–ROM GTITM, Plant Variety Database, 2006/04, GTI Jouve Retrieval Software, Citation for Malus 'Red Topaz' 3 pages.*

Institute of Experimental Botany, AV CR [online] [retrieved on Mar. 26, 2007]. Retrieved from the Internet <http://www.expats.cz/prague/czech/colleges.instituteofexperimentalbotanyavcr/> 2 pages.*

2002 and Succeeding Crop Years Eligible Plant List and Plant Price Schedule Nursery Crop Insurance Program [online] [retrieved on Mar. 28, 2007]. Retrieved from the Internet <http://www.rma.usda.gov/FTP/Applications/nursery_crop_ins._program/2002/books/co_book.pdf> p. 145.*

Plant Varieties Journal Quarter Two 2000 vol. 13, No. 2, Citation for Malus 'Mariri Red', pp. 37–38.*

* cited by examiner

*Primary Examiner*—Kent Bell
*Assistant Examiner*—June Hwu
(74) *Attorney, Agent, or Firm*—Stratton Ballew PLLC

(57) ABSTRACT

The 'Red Topaz' apple tree originated as a spontaneous limb sport mutation discovered on a 'Topaz' apple tree. 'Red Topaz' is distinguishable from its parent by its fruit. 'Red Topaz' has a solid red overcolor and matures about ten days earlier than 'Topaz.'

2 Drawing Sheets

Latin name of the genus and species of the plant claimed: *Malus domestica.*

Variety denomination: 'Red Topaz'.

BACKGROUND OF THE INVENTION

'Red Topaz' originated as a spontaneous mutation on a single limb of a 'Topaz' apple tree (not patented), discovered by the inventors in a cultivated apple orchard in Pencin u Liberce, Czech Republic in 1998. 'Red Topaz' was first asexually propagated by budding at Pencin u Liberce, Czech Republic in 1999, and has been shown to remain true to type over successive generations.

BRIEF SUMMARY OF THE INVENTION

'Red Topaz' is very similar to its parent 'Topaz,' but is clearly distinguishable from its parent by the appearance of its fruit. 'Red Topaz' develops a washed out red overcolor over its entire surface about 10 days earlier than its parent. The red overcolor of 'Topaz' typically covers only about 60 percent of the fruit surface.

'Red Topaz' can further be compared to and distinguished from 'Fugachee Fuji' (U.S. Plant Pat. No. 16,270). The fruit of 'Red Topaz' is similar in size and shape to the fruit of 'Fugachee Fuji,' but has a brighter red overcolor than 'Fugachee Fuji' and is sweet-tart, as compared to the sweeter flavor of 'Fugachee Fuji.' 'Red Topaz' is ready for harvest about two weeks before 'Fugachee Fuji.'

BRIEF DESCRIPTION OF THE PHOTOGRAPH

DETAILED BOTANICAL DESCRIPTION

Figure 1:
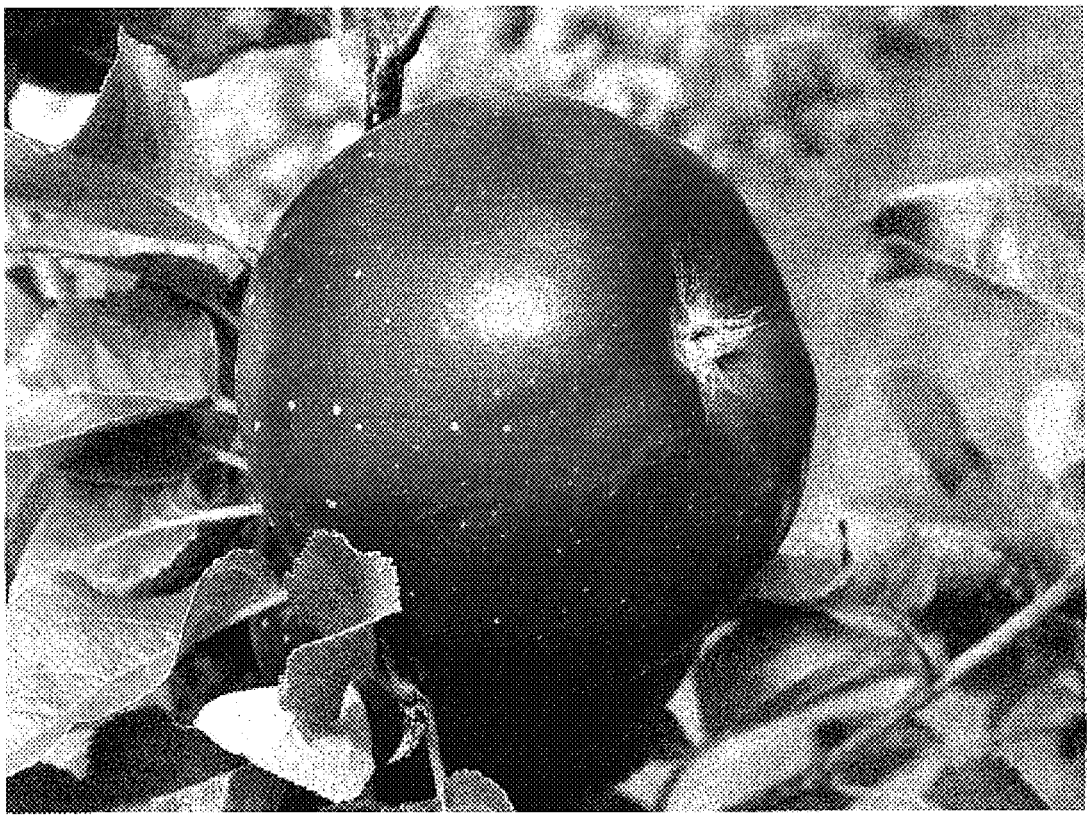
FIG. 1 shows the fruit and leaves of 'Red Topaz'.
Figure 2:
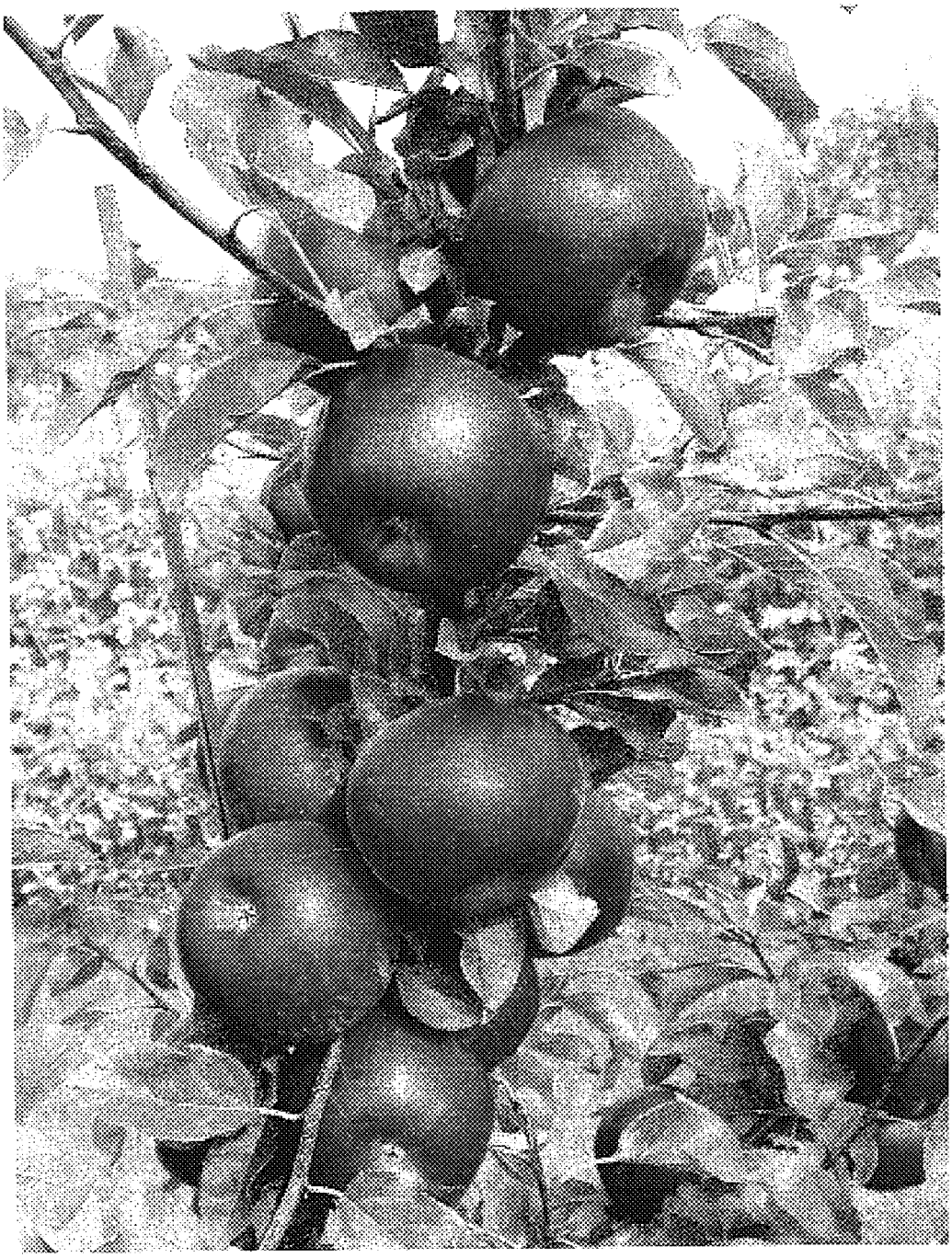
FIG. 2 shows the fruit, leaves and branches of 'Red Topaz'.

The following detailed botanical description is based on observations of four year old specimens grown at Pencin u Liberce, Czech Republic, as well as five year old specimens grown at Parker, Wash., USA on M26 rootstock. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Tree:
   *Vigor.*—Medium.
   *Type.*—Branched.

*Habit.*—Upright.
*Size.*—Height 3.3 m; spread 2.7 m.
*Trunk.*—Diameter 21 cm at soil level; bark texture smooth; color greyed-orange167A and greyed-green 197A; lenticels round, 2 to 3 mm diameter, white.
*Branch.*—Length 40.7 cm; diameter 2.8 cm; color greyed-orange 176B; lenticels round, 2 mm diameter, white.
*Winter hardiness.*—Hardy in area tested.

2. Dormant one-year-old shoot:
*Pubescence* (*on upper half of shoot*).—Medium.
*Size.*—Diameter 0.5 cm; length 29 cm.
*Color.*—Greyed-orange 176B.
*Length of internode.*—Short, 3 to 4 cm.
*Number of lenticels.*—Many, about 2.5 per $cm^2$.

3. Flowers:
*Bud.*—Quantity per spur 3 to 5; elongated; length 2 cm, diameter 1 cm; color (closed) red-purple 63A.
*Color of bud just before opening.*—Red-purple 63C.
*Flower size.*—Diameter 4 cm; quantity per cluster 3 to 5.
*Petals.*—Quantity per flower 5; length 2 cm; width 1.4 cm; apex shape rounded; base shape cuneate; margin smooth, overlapping; upper surface color red-purple 68A; lower surface color white 155D when fully open.
*Sepals.*—Quantity 5 per flower, length 1 cm; color green 138C.
*Reproductive organs.*—Pedicel — length 2 cm; diameter 2 mm; color green 144C; Pistil — length 1 cm; color green-white 157A; Anthers — quantity per flower 16, length 1 mm; pollen color yellow 1A; Stigma — length 1 mm; color yellow 1C; Style — length 9 mm; color green-white 157A; Ovary — Size 2 mm; color green 137B.
*Bloom period.*—First bloom April 10, full bloom April 17 (2007 growing season, Parker, Wash.).

4. Leaf:
*Attitude in relation to shoot.*—Outward, 50°.
*Size.*—Length 4 cm; width 2 cm; length-width ratio 2:1.
*Margin.*—Serrated.
*Shape.*—Elliptic; apex acuminate; base equilateral.
*Color.*—Upper surface green 144A; lower surface green 144A.

5. Petiole:
*Length.*—Short, 1 cm.
*Color.*—Red 51B to white N155B.

6. Fruit:
*Size.*—Medium to large, about 8 cm diameter.
*Ratio height to width.*—Small, 1:1.
*Position of max. width.*—At middle to top.
*Shape.*—Globose conical.
*Ribbing.*—Absent.
*Crowning at distal end.*—Weak.
*Aperture of eye.*—Closed.
*Size of eye.*—Medium, 1 cm.
*Length of sepal* (*visual*).—Short.
*Depth of eye basin.*—Shallow, 5 mm.
*Width of eye basin.*—Broad, 15 mm.
*Thickness of stalk.*—Thin, 0.2 cm.
*Length of stalk.*—Short, 2.1 cm.
*Depth of stalk cavity.*—Medium, 1 cm.
*Width of stalk cavity.*—Medium, 1 cm.
*Bloom of skin.*—Absent.
*Greasiness of skin.*—Weak.
*Ground color of skin.*—Yellow 151A.
*Over color of skin.*—Red 43C.
*Intensity of over color of skin.*—Medium.
*Percentage of over color of skin.*—100 percent.
*Type of over color of skin.*—Washed out.
*Russeting around eye basin.*—Absent or very low.
*Russeting on cheeks.*—Absent or very low.
*Russeting around stalk cavity.*—Absent or very low.
*Surface texture.*—Smooth.
*Size of lenticels.*—Medium, 2 mm.
*Firmness of the flesh* (*measurement with penetrometer*) .—Medium to firm.
*Texture of the flesh.*—Crisp, very juicy, not coarse.
*Ascorbic acid content.*—83 g/l.
*Color of the flesh.*—Cream 158B.
*Seed.*—Oval, brown 166B, length 0.7 cm, width 0.5 cm, quantity 5 per fruit.
*Aperture of locules (fruit in cross section).*—Half-open.
*Harvest date.*—Mid season, about 1 week before 'Golden Delicious'.
*Yield.*—Medium to medium heavy.
*Use.*—Fresh market.
*Storageability.*—Stores well in common cold storage.

Resistance/susceptibility: Moderate resistance to scab and powdery mildew.

It is claimed:

1. We claim a new and distinct apple tree substantially as shown and described herein.

* * * * *